United States Patent [19]

Richardson et al.

[11] 4,113,765

[45] Sep. 12, 1978

[54] CONTINUOUS PROCESS FOR SULFONATING ALKYL AROMATICS

[75] Inventors: Eugene E. Richardson, Aurora; Frank Sidorowicz, Naperville, both of Ill.

[73] Assignee: Standard Oil Company (Indiana), Chicago, Ill.

[21] Appl. No.: 741,842

[22] Filed: Nov. 15, 1976

Related U.S. Application Data

[63] Continuation-in-part of Ser. No. 560,639, Mar. 21, 1975, abandoned.

[51] Int. Cl.$^2$ ............................................ C07C 143/24
[52] U.S. Cl. ............................ 260/505 S; 260/505 C; 260/505 E
[58] Field of Search ............. 260/505 C, 505 E, 505 S

[56] References Cited

U.S. PATENT DOCUMENTS

| 2,448,184 | 8/1948 | Lemmon | 260/505 |
|---|---|---|---|
| 2,573,675 | 11/1951 | Bloch et al. | 260/505 |
| 2,768,199 | 10/1956 | Luntz et al. | 260/505 |
| 3,024,258 | 3/1962 | Brooks et al. | 260/505 |

*Primary Examiner*—A. Siegel
*Attorney, Agent, or Firm*—Thomas J. Connelly; Arthur G. Gilkes; William T. McClain

[57] ABSTRACT

Disclosed is a continuous process for the sulfonation of an alkylaromatic reactant involving heating liquid sulfur trioxide in a vaporizer and mixing this sulfur trioxide gas stream with a hexane-alkylaromatic stream containing about 1 to about 3 wt. % quantity of a promoter, which can be either sulfuric acid or an alkyl benzene sulfonic acid, in a sulfonator - static inline mixer, mixing water with the sulfonated product as it passes to the water reactor - static inline mixer, passing the aqueous sulfonated product through degassing column-heat exchanger apparatus and separating the sulfonated product from the aqueous sulfuric acid. The reaction is conducted under controlled temperature and pressure conditions.

23 Claims, 1 Drawing Figure

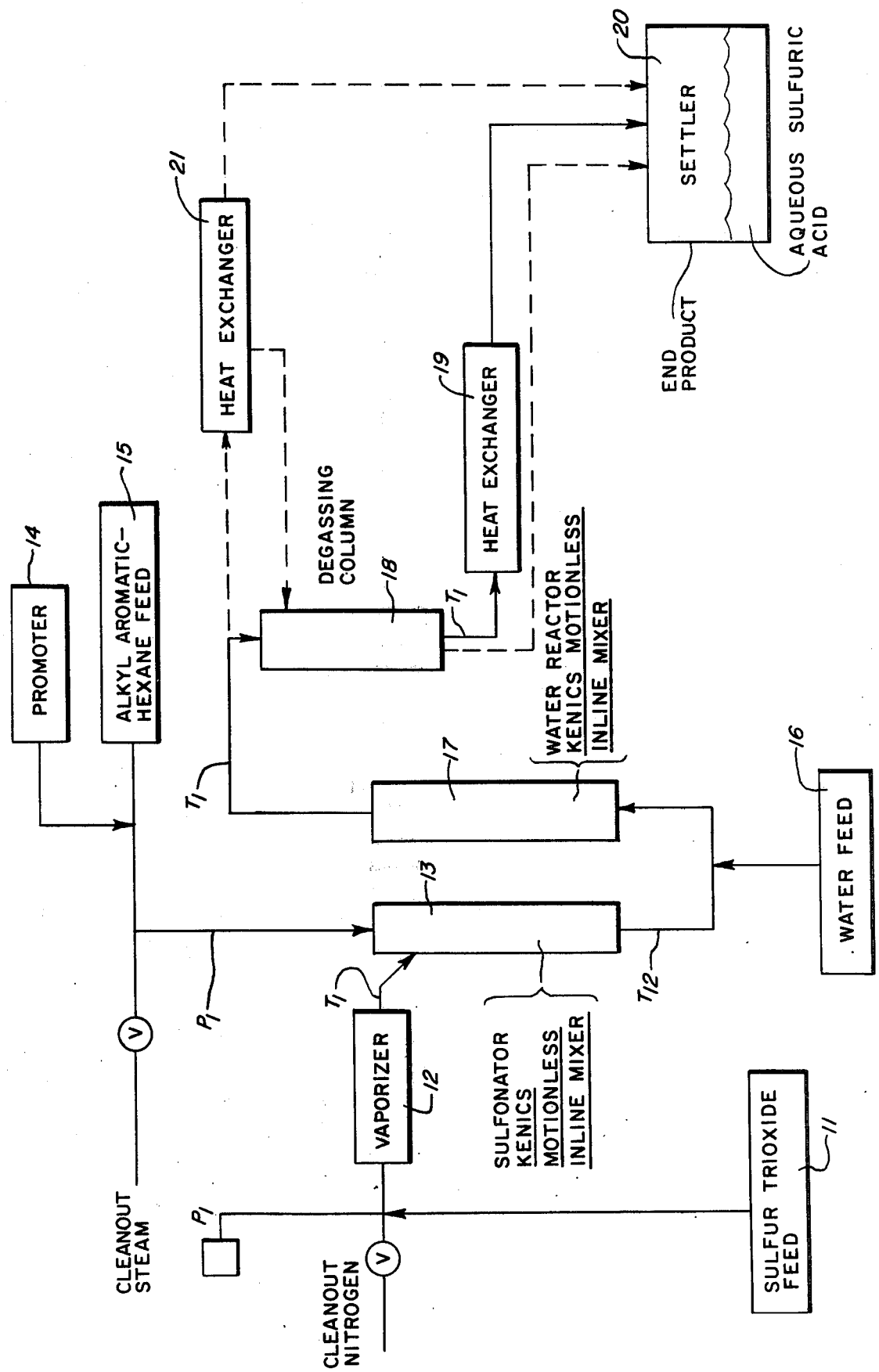

CONTINUOUS PROCESS FOR SULFONATING ALKYL AROMATICS

CROSS-REFRENCE TO RELATED APPLICATIONS

This application is a continuation-in-part of patent application, Ser. No. 560,639, filed Mar. 21, 1975, now abandoned.

BACKGROUND OF THE INVENTION

The preparation of organic sulfonic acids and of organic sulfonates for use as soaps, detergents and additives for lubricating oils is well known in the art. In the past, the sulfonation of alkylaromatic hydrocarbons has generally been carried out in batch operations. In these processes it was customary to employ a number of steps, the first of which was to sulfonate the hydrocarbon by treating it with a large excess of oleum in order to drive the reaction to completion. The second step was to dilute the mixture with water and stratify it in order to separate the sulfonic acid from the excess diluted sulfuric acid. The final phase consisted of converting the sulfonic acid to the sulfonate by neutralization. Due to the time factor involved, efforts have been made to develop continuous sulfonation processes, such as one in which the acid flows counter-currently to an excess of the hydrocarbon in liquid phase, and another in which an excess of preheated acid flows counter-currently to a stream of the hydrocarbon vapors. Up until the present time, however, a continuous process for the sulfonation of such hydrocarbons has not been considered commercially practical. One of the major drawbacks has been the buildup of sludge (residual sulfuric acid) which is a disfavorable substance in these particular reactions. Attempts have been made to cut back on the formation of this residual sulfuric acid by employing sulfonating agents other than oleum but with little success. Although the presence of sulfuric acid in the product could be eliminated, the resulting product would still exhibit a number of undesirable characteristics. An example is the use of liquid sulfur trioxide as the sulfonating agent in which the resulting product exhibited a pH drift to the acid side after apparent neutralization and also contained an off odor. In our quest to formulate a quicker and more favorable process we have invented a continuous process for the sulfonation of aromatic hydrocarbons which also has the desirable characteristic of little or no sludge formation.

The term "alkyl benzene sulfonic acid" as used throughout this application can encompass almost any alkylaromatic and includes such sulfonic acids as polypropylene benzene sulfonic acid and polybutene-1 benzene sulfonic acid. The polypropyl radical of the polypropyl benzene sulfonic acid generally has a molecular range selected from approximately between 350 and 1,200.

The polybutene-1 radical of the polybutene-1 benzene sulfonic acid preferably has a molecular weight range of about 350 to 600. Currently, many of the processes taught by the prior art describe a method whereby the liquid sulfur trioxide sulfonating agent is diluted with an inert gas in the initial step. Contrary to these procedures, our system does not necessitate this dilution action. It should also be noted that our sulfonator - static inline mixer — approximates plug flow in a manner facilitating the reduction of possible sludge formation. It is significant in that since there are no moving parts in the sulfonator — static inline mixer, the capital and operating costs are relatively low.

"Static inline mixer" as used throughout this application refers to a motionless mixing device or static mixer such as the Kenics motionless inline mixer or the Koch mixer. Our experimental tests were conducted using Kenics static mixers and these particular mixers are described in the following publications:

(1) U.S. Pat. No. 3,286,992, issued Nov. 22, 1966.
(2) The article entitled "Motionless Inline Mixers Stir Up Broad Interest" appearing in the May 19, 1969 issue of Chemical Engineering.

A view of the prior art includes use of gaseous sulfur trioxide diluted with inert gas in falling film reactors (U.S. Pat. Nos. 3,328,460 and 3,529,645); batch process sulfonation (U.S. Pat. Nos. 3,056,831 and 3,248,413); countercurrent extraction processes with or without sulfuric acid present (U.S. Pat. Nos. 3,677,934 and 3,798,261); sulfonation in the presence of inorganic sulfites (U.S. Pat. No. 3,789,067) and processes requiring the presence of 10% sulfuric acid (British Pat. No. 669,899, issued in 1952). None of the processes of the prior art involve the use of a sulfonator, which is a "static inline mixer" in the manner employed in our process.

SUMMARY OF THE INVENTION

According to this invention, there is provided a continuous process for the sulfonation of alkylaromatics, containing about 1 to about 3 wt.% quantity of a promoter, in a manner resulting in high yield with little or no sludge formation. Commonly about 1 wt.% quantity of a promoter is used. More specifically, this continuous process involves the sulfonation of an alkylaromatic reactant by introducing liquid sulfur trioxide into a vaporizer and therein heating to a temperature ranging from about 120° to about 160° F. at a pressure ranging from about 10 to about 70 psi. The undiluted vaporized (gaseous) sulfur trioxide stream is directed to a sulfonator — static inline mixer — wherein the sulfur trioxide stream reacts with the alkylaromatic of the reactant stream, consisting of an inert solvent a solution such as a hexane solution of an alkylaromatic reactant containing about 1 to about 3 wt.% quantity of a promoter, which can be either sulfuric acid or an alkyl benzene sulfonic acid. Utilizing a sulfonator of the static inline mixer variety makes it possible to direct the alkylaromatic feed stream into the top section of the mixer and introduce the stream of sulfur trioxide gas from the side. This is desirable in that it cuts down on the amount of sludge formation when the two streams come into contact and also assures that the reaction is more uniformly carried out. Experimentation has also shown that it is favorable to add the sulfur trioxide gas from the side at a level approximately equal to the third mixing element of the static inline mixer. This tends to allow the alkylaromatic feed to enter into the mixing motion before it combines with the ($SO_3$) gas and seems to present a better mixing environment. The promoter generally does not lose its identity during the reaction between the gaseous sulfur trioxide and the feed (i.e. alkylaromatic hexane solution) but instead only acts to start the reaction. The product resulting from reacting the gaseous sulfur trioxide stream and the reaction product stream, having a temperature of approximately between 130° and 200° F., is admixed with water as it passes to the water reactor - static inline mixer. The water is introduced into the reaction product stream at a rate sufficient to react with the excess SO₃ left over from the initial reaction to form an aqueous solution of approximately between 76% and 92% sulfuric acid, preferably 85% sulfuric acid. If sulfuric acid is used as the promoter in the first reaction, a very small additional amount of sulfuric acid will be formed when the excess sulfur trioxide reacts with the water. If a sulfonic acid is used as a promoter in the first reaction, this sulfonic acid will usually dissolve into the new sulfonic product produced by the first reaction but there will generally be some excess (SO₃) left over after this first reaction to react with the added water to form a very small amount of sulfuric acid. Therefore, a very small amount of sulfuric acid will be present regardless of which promoter is used.

The aqueous reaction product, having a temperature ranging from about 130° to about 200° F., preferably about 150° to about 168° F. and pressure ranging from about 2.5 to about 5.5 psi, is cooled to a temperature of about 140° F. by passing it through a degassing column-heat exchanger apparatus. It should be noted that as the reaction product temperature is raised, the corresponding pressure could also increase above the 5.5 psi stated in the previous sentence. Any combination of degassing column and/or heat exchanger will suffice but the preferable arrangement is to pass the product through a degassing column to draw off sulfur dioxide gas and then cool the stream by passing it through a heat exchanger. The purpose of the heat exchanger is to reduce the temperature below the boiling point of the solvent, (i.e.) hexane. The stream is directed from the heat exchanger into the settler where the sulfonated product is allowed to separate from the aqueous sulfuric acid.

Generally the alkylaromatics include polypropylene, polybutene-1, and propylene-butene-1 derivatives of benzene wherein the alkyl moiety has a molecular weight within the range of about 350 to about 1,200. The preferable molecular weight consists of the range between 350 and 1,000 and the more preferable range is from 400 to 900.

By practicing the process of this invention, therefore, the continuous production of a sulfonated alkylaromatic in high yield with little or no sludge formation is achieved.

DESCRIPTION OF THE PREFERRED EMBODIMENTS

Organic compounds within the broad class of alkylaromatics include such compounds as (a) polypropylene aromatics, (b) polybutene-1 aromatics, (c) polyisobutylene aromatics, (d) poly-n-butylene aromatics, (e) polyethylene aromatics, (f) propylene-butene-1 aromatics, (g) propylene-isobutylene aromatics, (h) propylene-n-butylene aromatics, (i) propylene-ethylene aromatics, (j) ethylene-butene-1 aromatics, (k) ethylene-isobutylene aromatics, (l) ethylene-n-butylene aromatics, (m) butene-1-isobutylene aromatics, (n) butene-1-n-butylene aromatics and (o) isobutylene-n-butylene aromatics.

The term "aromatics" as used hereinabove and throughout this application is intended to include mono- and polycyclic aromatic hydrocarbons such as benzenes, naphthalenes and anthracenes, preferably benzenes.

The preferred alkylaromatics include polypropylene, polybutene-1, and propylene-butene-1 derivatives of benzene wherein the alkyl moiety generally has a molecular weight within the range of about 300 to about 1,200. Especially preferred are polypropylene benzenes wherein the alkyl moiety has a molecular weight range of about 350 to about 1,000 and polybutene-1 benzenes wherein the alkyl moiety has a molecular weight range of about 350 to 600.

The aromatic hydrocarbon may be mono, di or tri-substituted, but is most commonly mono-substituted.

The sulfonating agent utilized in the present process which produces the sulfonic acid derivative of the alkylaromatic charged to the process is most commonly undiluted gaseous sulfur trioxide.

The promoter utilized in this process can be either sulfuric acid or an alkyl benzene sulfonic acid but is employed only in small amounts, such as about 1 to about 3 wt.% quantity of promoter.

The term "alkyl benzene sulfonic acid" as used throughout this application can encompass almost any alkylaromatic and includes such sulfonic acids as polypropylene benzene sulfonic acid and polybutene-1 benzene sulfonic acid. Alkyl benzene sulfonic acids are commercially available.

The inert solvent, for the alkylaromatic reactants, employed in the process of the present invention is hexane but could be any other inert solvent known in the art, such as carbon tetrachloride, pentane or heptane.

The drawing depicts a schematic diagram of the steps involved in a continuous process for sulfonating alkylaromatics. The alkylaromatic of the type referred to in this application can be sulfonated in accordance with the continuous process as described in this invention. In such an operation the liquid sulfur trioxide feed 11 is introduced into a vaporizer 12 and therein heated to a temperature within the range of about 120° to about 160° F. at a pressure ranging from about 10 to about 70 psi. The undiluted vaporized (gaseous) sulfur trioxide stream is directed to a sulfonator - static inline mixer 13 wherein the sulfur trioxide stream reacts with the alkylaromatic-hexane reactant stream from 15 which contains about 1 to about 3 wt.% quantity of a promoter 14. The product resulting from reacting the sulfur trioxide stream and the reactant stream, having a temperature of approximately between 130° and 200° F., is admixed with water from a water feed 16 prior to entering water reactor — static inline mixer 17. The aqueous reaction product, having a temperature ranging from about 130° to about 200° F, and pressure ranging from about 2.5 to about 5.5 psi, is passed to degassing column 18 to remove sulfur dioxide gas and is thereafter cooled to a temperature of about 140° F. by passing it through heat exchanger 19 before the reaction product is passed to settler 20. In settler 20 the reaction product is allowed to separate from the aqueous sulfuric acid.

This invention contemplates that the aqueous sulfonated alkylaromatic product from water reactor 17 can either (a) pass through degassing column 18, then through heat exchanger 19; or (b) pass through heat exchanger 21, then degassing column 18, then heat exchanger 19; or (c) pass through heat exchanger 21, then degassing column 18; or (d) pass through heat exchanger 21 only, en route to settler 20.

The following Table depicts the kind and size of equipment used to demonstrate this invention and describes the various symbols (notation) listed on the drawing.

TABLE

A CONTINUOUS PROCESS FOR SULFONATING ALKYL AROMATICS

Describes Equipment Used to Demonstrate This Invention and Notation as Depicted on the Drawing

| Equipment Description | |
|---|---|
| Vaporizer-24" of ¼"SS tubing jacketed with steam | TI-Temperature Indicator |
| Sulfonator - ⅛ — glass Kenics motionless inline mixer with SO₃ inlet at sidearm at the third element | PI - Pressure Indicator |
| Water Reactor - ¼" glass Kenics motionless inline mixer | V - Valve |
| Heat Exchanger No. 1 - 6"spiral glass condenser | |
| Degasser - 100 ml. graduated cylinder fitted with a reflux condenser | |
| Settler - batch settling used in the Examples | |

EXAMPLES

The following examples are illustrative, without implied limitation, of our invention.

EXAMPLE I

No sulfur acid was added to the polypropylene benzene reactant.

Liquid sulfur trioxide was introduced at a rate of 8.3 ml/minute (0.20 moles/minute equivalent to 2 moles/mole of active polypropylene benzene reactant) into the vaporizer and heated to between 120° and 123° F. at between 42 and 46 psi, then mixed with 196 ml/minute (0.10 moles active polypropylene benzene reactant/minute) of a 50 wt.% hexane solution of 81% active polypropylbenzene (molecular wt. ranging from 580 to 600) in the sulfonator. The reaction product from the sulfonator at 156° F. and 2.5 to 3.0 psi was admixed with water as it flowed to the water reactor. The water was introduced into the reaction product stream at a rate of 3.6 ml/minute (0.20 mole/minute equivalent to 2 moles/mole of excess sulfur trioxide). The aqueous reaction product at 150° F. and 2.5 to 3.0 psi was passed through a heat exchanger wherein the temperature was reduced to 140° F. and then through a degassing column-heat exchanger apparatus before passing to a batch settler in which the sulfuric acid formed in the water reactor was separated. Our feed of polypropylene benzene contains some polypropylene which is insert to the reaction that takes place in the sulfonator. This accounts for the fact that the end product which is analyzed contains a percentage of unreacted polypropylene and polypropylene benzene.

The final product analyzed:

| | |
|---|---|
| Sulfonic acid | 26.7% |
| Sulfuric acid | 1.0% |
| Hexane | 45.5% |
| Unreacted polypropylene and polypropylene benzene | 26.7% |
| Conversion* | 63.0% |

*Conversion was calculated from the moles of sulfonic acid formed/mole of active polypropylene benzene charged. This procedure was used to calculate the conversion percentage in all of the Examples. The value for conversion appears slightly over 100% in examples II and IV due to the inability of the measuring instruments to record with sufficient accuracy.

EXAMPLE II

The procedure of Example I was repeated with 1 wt.% concentrated sulfuric acid added to the polypropylene benzene-hexane solution. The temperatures and pressures observed were:

| | |
|---|---|
| Vaporizer | |
| Temperature | 130° F. |
| Pressure | 57–60 psi |
| Sulfonator | |
| Temperature | 170° F. |
| Pressure | 3.5–4.5 psi |
| The product analyzed: | |
| Sulfonic acid | 43.4% |
| Sulfuric acid | 4.7% |
| Hexane | 44.5% |
| Unreacted polypropylene and polypropylene benzene | 8.5% |
| Conversion | 103% |

EXAMPLE III

The procedure of Example I was repeated with 3 wt.% of polypropylene benzene sulfonic acid solution* (molecular wt. range for polypropylene moiety was 580 to 600) added to the polypropylene benzene-hexane solution. The sulfur trioxide rate was reduced to 7.85 ml/minute (0.189 mole/minute or 1.9 moles/mole of active polypropylene benzene). Since the water rate was not changed, the ratio of water to excess sulfur trioxide increased to 2.2 moles/mole. The temperature and pressures observed were:

| | |
|---|---|
| Vaporizer | |
| Temperature | 130° F. |
| Pressure | 56 psi |
| Sulfonator | |
| Temperature | 175° F. |
| Pressure | 5–6 psi |
| *Analysis of the polypropylene benzene sulfonic acid promoter was: | |
| Sulfonic acid | 55.2% |
| Sulfuric acid | 1.5% |
| Hexane | 31.0% |
| Polypropylene polymer | 12.2% |
| The product analyzed: | |
| Sulfonic acid | 45.9% |
| Sulfuric acid | 2.2% |
| Hexane | 41.6% |
| Unreacted polypropylene and polypropylene benzene | 10.3% |
| Conversion | 100% |

EXAMPLE IV

Liquid SO₃ was introduced at a rate of 7.8 ml./min. (1.9 moles/mole active polybutene-1 benzene) into the vaporizer and heated to 133° F. at 61 to 66 psi, then mixed with 196 ml./min. (0.10 moles active polybutene-1 benzene/min.) of a 50 wt.% hexane solution of 84% active polybutene-1 benzene containing 1 wt.% H₂SO₄ in the sulfonator. The reaction product from the sulfonator at 168° F. and 4.5 to 5.5 psi was admixed with a water stream as it flowed to the water reactor at 164° F. and 4.5 to 5.5 psi. The aqueous reaction product was passed through a heat exchanger and through a degassing column-heat exchanger apparatus before passing to a batch settler in which the sulfuric acid was separated. Our feed of polybutene-1 benzene contains some polybutene-1 which is inert to the reaction that takes place in the sulfonator. This accounts for the fact that the end product which is analyzed contains a percentage of unreacted polybutene-1 and polybutene-1 benzenes. Product analyzed:

| | |
|---|---|
| Sulfonic acid | 46.4% |
| Unreacted polybutene-1 + polybutene-1 benzene* | 8.4% |

-continued

| | |
|---|---|
| Conversion | 105% |

*Polybutene-1 or the polybutene-1 radical referred to in Examples IV and V had a molecular weight range of 400-500.

EXAMPLE V

The procedure of Example IV was repeated with 3 wt.% polybutene-1 sulfonic acid added to the polybutene-1 benzene-hexane solution. Temperatures and pressures observed were:

| | |
|---|---|
| Vaporizer | |
| Temperature | 139° F. |
| Pressure | 61–65 psi |
| Sulfonator | |
| Temperture | 169° F. |
| Pressure | 5–6 psi |
| Product analyzed: | |
| Sulfonic acid | 46.6% |
| Unreacted polybutene-1 + polybutene-1 benzene | 10.9% |
| Conversion | 100% |

EXAMPLE VI

The procedure of Example IV was repeated with a 50 wt.% hexane solution of 68% active polypropylbenzene* containing 1 wt.% $H_2SO_4$. Flow rates were held the same resulting in an increase in the $SO_3$ molar ratio to 2.15 moles $SO_3$/mole active alkylate. Temperatures and pressures observed were:

| | |
|---|---|
| Vaporizer temperature | 140° F. |
| Vaporizer pressure | 61–71 psi |
| Product analyzed: | |
| Sulfonic acid | 36.0% |
| Unreacted polypropylene polymer + polypropylbenzene | 16.6% |
| Conversion | 101% |

*Polypropylene or the polypropyl radical referred to in Examples VI and VII had a molecular wt. range of 800–850.

EXAMPLE VII

The procedure of Example VI was repeated with 3 wt.% polypropylbenzene sulfonic acid added to the polypropylene benzene-hexane solution. Temperatures observed were:

| | |
|---|---|
| Vaporizer temperature | 142° F. |
| Sulfonator temperature | 160° F. |
| Product analyzed: | |
| Sulfonic acid | 35.5% |
| Unreacted polymer + alkylate | 17.6% |
| Conversion | 99% |

We claim:

1. A continuous process for the sulfonation of an alkylaromatic reactant, comprising the following steps:
   (a) introducing liquid sulfur trioxide into a vaporizer and heating to a temperature ranging from about 120° F. to about 160° F. at a pressure ranging from about 10 psi to about 70 psi;
   (b) mixing a sulfonator - static inline mixer (1) a stream of sulfur trioxide gas produced in step (a) and (2) a reactant stream, comprising an inert solvent solution of the alkylaromatic reactant containing a promoter of about 1 wt.% to about 3 wt.% quantity of sulfuric acid;
   (c) mixing the product from step (b), having a temperature of between approximately 130° F. and about 200° F., with water which is introduced into the system as the product passes to a static inline mixer thereby forming an aqueous solution comprising a sulfonation product and aqueous sulfuric acid;
   (d) passing the product from step (c) at a pressure ranging from about 2.5 psi to about 5.5 psi through a heat exchanger to produce an aqueous solution comprising a sulfonation product and aqueous sulfuric acid at about 140° F.; and
   (e) separating the sulfonation product from the aqueous sulfuric acid.

2. The process of claim 1 wherein the product from step (c) is passed through a degassing column.

3. The process of claim 1 wherein the product from step (d) is passed through a degassing column.

4. The process of claim 1 wherein the alkylaromatic reactant is selected from the group consisting of (a) polypropylene aromatics, (b) polybutene-1 aromatics, (c) polyisobutylene aromatics, (d) poly-n-butylene aromatics, (e) polyethylene aromatics, (f) propylene-butene-1 aromatics, (g) propylene-isobutylene aromatics, (h) propylene-n-butylene aromatics, (i) propylene-ethylene aromaics, (j) ethylene-butene-1 aromatics, (k) ethylene isobutylene aromatics, (l) ethylene-n-butylene aromatics, (m) butene-1 isobutylene aromatics, (n) butene-1-n-butylene aromatics and (o) isobutylene-n-butylene aromatics.

5. The process of claim 1 wherein the alkylaromatic is selected from the group consisting of (a) alkyl benzenes, (b) alkyl naphthalenes and (c) alkyl anthracenes.

6. The process of claim 1 wherein the stream of sulfur trioxide gas enters the sulfonator - static inline mixer — from the side section whereas the reactant stream enters the sulfonator — static inline mixer - from the top section.

7. The process of claim 1 wherein the alkylaromatic is selected from the group consisting of: (a) polypropylene benzenes and (b) poly-butene-1 benzenes.

8. The process of claim 5 wherein the alkyl moiety of the alkylaromatic has a molecular weight within the range of 350 and 1200.

9. The process of claim 1 wherein the alkylaromatic comprises a polypropylene benzene and the alkyl moiety has a molecular weight within the range of about 350 to about 1,000.

10. The process of claim 1 wherein the reactant stream comprises a 50 wt.% solution of polybutene-1 alkylate of benzene, the polybutene-1 moiety having a molecular weight range of 350 to 600 and the reactant stream containing 1 wt.% sulfuric acid.

11. The process of claim 1 wherein the reactant stream comprises a 50 wt.% solution of polypropylene alkylate of benzene, the polypropylene moiety having a molecular weight range of 350 to 1,000 and the reactant stream containing 1 wt.% sulfuric acid.

12. A continuous process for the sulfonation of an alkylaromatic reactant, comprising the following steps:
   (a) introducing liquid sulfur trioxide into a vaporizer and heating to a temperature ranging from about 120° F. to about 160° F. at a pressure ranging from about 10 psi to about 70 psi;
   (b) mixing in a sulfonator - static inline mixer (1) a stream of sulfur trioxide gas produced in step (a) and (2) a reactant stream, comprising an inert solvent solution of the alkylaromatic reactant containing a promoter of about 1 wt.% to about 3 wt.% quantity of an alkyl benzene sulfonic acid;

(c) mixing the product from step (b), having a temperature of between approximately 130° F. and about 200° F., with water which is introduced into the system as the product passes to a static inline mixer thereby forming an aqueous solution comprising a sulfonation product and aqueous sulfuric acid;

(d) passing the product from step (c) at a pressure ranging from about 2.5 psi to about 5.5 psi through a heat exchanger to produce an aqueous solution comprising a sulfonation product and and aqueous sulfuric acid at about 140° F.; and (e) separating the sulfonation product from the aqueous sulfuric acid.

13. The process of claim 12 wherein the product from step (c) is passed through a degassing column.

14. The process of claim 12 wherein the product from step (d) is passed through a degassing column.

15. The process of claim 12 wherein the alkylaromatic reactant is selected from the group consisting of (a) polypropylene aromatics, (b) polybutene-1 aromatics, (c) polyisobutylene aromatics, (d) poly-n-butylene aromatics, (e) polyethylene aromatics, (f) propylene-butene-1 aromatics, (g) propylene-isobutylene aromatics, (h) propylene-n-butylene aromatics, (i) propylene-ethylene aromatics, (j) ethylene-butene-1 aromatics, (k) ethylene isobutylene aromatics, (l) ethylene-n-butylene aromatics, (m) butene-1 isobutylene aromatics, (n) butene-1-n-butylene aromatics and (o) isobutylene-n-butylene aromatics.

16. The process of claim 12 wherein the alkylaromatic is selected from the group consisting of (a) alkyl benzenes, (b) alkyl naphthalenes and (c) alkyl anthracenes.

17. The process of claim 12 wherein the stream of sulfur trioxide gas enters the sulfonator — static inline mixer — from the side section whereas the reactant stream enters the sulfonator — static inline mixer — from the top section.

18. The process of claim 12 wherein the alkylaromatic is selected from the group consisting of: (a) polypropylene benzenes and (b) polybutene-1 benzenes.

19. The process of claim 16 wherein the alkyl moiety of the alkylaromatic has a molecular weight within the range of 350 and 1200.

20. The process of claim 12 wherein the alkylaromatic comprises a polypropylene benzene and the alkyl moiety has a molecular weight within the range of 350 to 1,000.

21. The process of claim 12 wherein the reactant stream comprises a 50 wt.% solution of polybutene-1 alkylate of benzene, the polybutene-1 moiety having a molecular weight of 350 to 600 and the reactant stream containing 3 wt.% polybutene-1 benzene sulfonic acid.

22. The process of claim 12 wherein the reactant stream comprises a 50 wt.% solution of polypropylene alkylate of benzene, the polypropylene moiety having a molecular weight range of 350 to 1,000 and the reactant stream containing 3 wt.% of a polypropylene benzene sulfonic acid.

23. A continuous process for the sulfonation of an alkylaromatic reactant, comprising the following steps:

(a) introducing liquid sulfur trioxide into a vaporizer and heating to a temperature ranging from about 120° F. to about 160° F. at a pressure ranging from about 10 psi to about 70 psi;

(b) mixing in a sulfonator - static inline mixer (1) a stream of sulfur trioxide gas produced in step (a) and (2) a reactant stream, comprising an inert solvent solution of the alkylaromatic reactant containing a promoter of about 1 wt.% to about 3 wt.% quantity of sulfuric acid;

(c) mixing the product from step (b), having a temperature of between approximately 150° F. and about 168° F., with water which is introduced into the system as the product passes to a static inline mixer thereby forming an aqueous solution comprising a sulfonation product and aqueous sulfuric acid;

(d) cooling the product from step (c), having a pressure ranging from about 2.5 psi to about 5.5 psi, by passing it through a heat exchanger wherein the temperature is reduced to about 140° F.; and (e) separating the sulfonation product from the aqueous sulfuric acid.

* * * * *

UNITED STATES PATENT OFFICE
CERTIFICATE OF CORRECTION

Patent No. 4,113,765                    Dated September 12, 1978

Inventor(s) Eugene E. Richardson and Frank Sidorowicz

It is certified that error appears in the above-identified patent and that said Letters Patent are hereby corrected as shown below:

| Column | Line | |
|---|---|---|
| 5 | 9  | "-1/4-" should be -- -1/4" -- . |
| 5 | 27 | "moles/-" should be -- moles/ -- . |
| 5 | 46 | "insert" should be -- inert -- . |
| 7 | 61 | "mixing a" should be -- mixing in a -- . |
| 8 | 23 | "aromaics" should be -- aromatics -- . |
| 9 | 11 | *"and and" should be -- and an -- . |

Signed and Sealed this

Nineteenth Day of June 1979

[SEAL]

Attest:

RUTH C. MASON
Attesting Officer

DONALD W. BANNER
Commissioner of Patents and Trademarks